US00PP11500P

United States Patent [19]

Olesen et al.

[11] Patent Number: Plant 11,500

[45] Date of Patent: Sep. 5, 2000

[54] MINIATURE ROSE PLANT NAMED 'POULWEN'

[76] Inventors: L. Pernille Olesen; Mogens N. Olesen, both of Hillerødvejen 49, DK-3480, Fredensborg, Denmark

[21] Appl. No.: 09/123,879

[22] Filed: Jul. 27, 1998

[51] Int. Cl.[7] ..... A01H 5/00

[52] U.S. Cl. ..... Plt./116

[58] Field of Search ..... Plt./116, 118, 119

[56] References Cited

PUBLICATIONS

UPOU–ROM, Feb. 1999, Plant Variety Database, GTI Jouve Retrieval Software, Citation for 'POULwen'.

*Primary Examiner*—Howard J. Locker

[57] ABSTRACT

A new miniature rose plant which has abundant flowers and attractive foliage. The variety successfully propagates from softwood cuttings and is suitable for year round production in commerical glasshouses. This new and distinct variety has shown to be uniform and stable in the resulting generations from asexual propagation.

1 Drawing Sheet

SUMMARY OF THE INVENTION

The present invention constitutes a new and distinct variety of a miniature pot rose plant which originated from a controlled crossing between an unnamed seedling and 'POULdyb' an unpatented rose with red flowers. The two parents were crossed and the resulting seed was planted in a controlled environment. The new variety is named 'POULwen'.

The new rose may be distinguished from its seed parent, an unnamed seedling by the same inventors, by the following combination of characteristics:

1. 'POULwen' is a miniature rose variety with bronze-colored blooms, whereas the seed parent, an unnamed seedling, is a miniature rose with yellow petals and red intonations.

2. The plant of 'POULwen' is smaller in size and more even in growth as compared to the seed parent.

3. The flowers of 'POULwen' have greater longevity than the flowers of the seed parent.

4. The unnamed seed plant is an offspring of 'Mini-Poul', a red and yellow patio rose.

The new variety may be distinguished from its pollen parent, 'POULdyb', by the following combination of characteristics:

1. 'POULwen' is a miniature rose with bronze colored blooms, while 'POULdyb' is a patio rose with dark red blooms.

2. 'POULwen' has more flowers per plant and fewer petals than 'POULdyb'.

3. The flowers and foliage of 'POULwen' are smaller than 'POULdyb'.

4. 'POULwen' is compact in growth while 'POULdyb' is spreading.

3. 'POULdyb' is an offspring of 'RUImired', U.S. Plant Pat. No. 5,770 granted Jul. 22, 1986; 'POULtex', U.S. Plant Pat. No. 6,261 granted Aug. 30, 1988; and an unnamed yellow patio rose.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

This combination of qualities was not present in previously available commercial cultivars of this type and distinguish 'POULwen' from all other varieties of which we are aware.

As part of their rose development program, L. Pernille and Mogens N. Olesen germinated the seeds from the aformentioned hybridization and conducted evaluations on the resulting seedlings in a controlled environment in Fredensborg, Denmark.

'POULwen' was selected as a single plant from the progeny of the crossing of unnamed seedling and 'POULdyb'.

Asexual reproduction of 'POULwen' by cuttings and traditional budding was first done by L. Pernille and Mogens N. Olesen in their nursery in Fredensborg, Denmark in August, 1996. This initial and other subsequent propagations have demonstrated that the characteristics of 'POULwen' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULwen'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAIL DESCRIPTION OF THE VARIETY

The following is a detaied description of 'POULwen', as observed in its growth in glasshouses in Fredensborg, Denmark and Half Moon Bay, Calif. and in field nursery in Jackson County, Oreg. Color references are made using The Royal Horticultural Society (London, England) Colour Chart, 1995, except where common terms of color are used.

For a comparison, the nerarest existing rose variety is 'POULgelb', a patented variety described and illustrated in U.S. Plant Pat. No. 9,401 and issued on Dec. 19, 1995. Chart 1 details several physical characteristics of 'POULwen' and 'POULgelb'.

CHART 1

| | 'POULwen' | 'POULgelb' |
|---|---|---|
| Bud color at ¼ open | Blend of Yellow-Orange Group 15C and Orange-Red Group 30B | Yellow Group 12B |
| Upper surface of petal, open bloom | Yellow Group 13B with intonations of Orange-Red Group 32B | Yellow Group 13C |
| Reverse surface of petal, open bloom | Yellow Group 13B with intonations of Orange-Red Group 32B | Yellow Group 13C |
| Petalage | 40–50 petals under normal conditions | 35–40 petals under normal conditions |

Parents: Unnamed seedling×'POULdyb'.

Classification:

*Botanical.*—*Rosa hybrida*.

*Commercial.*—Miniature.

FLOWER AND FLOWER BUD

Blooming habit: Continuous.

Flower bud:

*Size.*—Upon opening, 16–18 mm in length from the base of receptacle to tip of bud.

*Bud form.*—Globular.

*Bud color.*—As the sepals part, the reverse surface of the petals is a blend of Yellow-Orange Group 15C and Orange Group 30B; except where exposed to bright light. When exposed to bright light, the reverse surface of the petal is Red Group 50A. Blend of Yellow-Orange Group 15C and Orange Group 30B at ¼ opening.

*Sepals.*—Green Group 143C. Weak foliaceous appendages on three of the five sepals. Surfaces of sepals moderately pubescent. Stipitate glands on sepals.

*Peduncle.*—Surface: Moderate number of stipitate glands present. Length: 18–25 mm average length. Color: Green Group 143C. Prickles: None.

*Receptacle.*—Surface: Smooth. Shape: Broadly urn-shaped. Size: Medium 6 mm (h)×10mm (w). Color: Green Group 143C.

*Borne.*—Usually borne Singularly.

Flower bloom:

*Diameter.*—Medium to large for a 10 cm pot rose. Average diameter is 45–50 mm.

*Form.*—Shape of flower when viewed from the side: Upon opening, upper part: Flattened convex. Upon opening, lower part: Flattened convex. Open flower, upper part: Flat. Open flower, lower part: Flat.

*Petalage.*—Double. Outermost petals reflex outwardly and form a double point. Average range: 40–50 under normal conditions.

*Color.*—Upon opening, middle zone of the upper surface of the petal is Yellow Group 13B. The margin of the upper surface has intonations of Orange-Red Group 32B. Upon opening, middle zone of the reverse surface of the petal is Yellow-Green Group 13B. Where exposed to bright light, the reverse surface of the outermost petals has moderate to strong intonations of Red Group 50A. The marginal zone has intonations of Orange-Red Group 32b. After opening, middle zone of the upper surface of the petal is Yellow Group 13B. After opening, middle zone and marginal zone of the reverse surface of the petal is Yellow Group 13B with intonations of Orange-Red Group 32B. A petal spot of Yellow Group 13B exists on the inner and outer sides of the bases of the petals

*General tonality.*—No change in the general tonality at the end of the first day. At the end of the fourth day, there is a change to Yellow Group Group 9C.

*Petal reflex.*—Outermost petals double reflexed.

*Petal edge.*—Smooth.

*Petaloids.*—Present. Commonly 5–10.

*Fragrance.*—Light.

*Duration.*—As a pot plant, flowers last from 10 to 12 days. As a cut flower 6 to 8 days.

Petals:

*Texture.*—Average.

*Shape.*—Round.

*Arrangement.*—Imbricated.

Reproductive organs: Floral parts often limited or lacking.

*Pollen.*—Color: Yellow Group 12A early on. Orange Group 26A as bloom opens. Abundance: Very limited.

*Anthers.*—Abundance: Very limited. Color: Yellow Group 12C.

*Filaments.*—Abundance: Very limited. Color: Yellow Group 12C.

*Stigmas.*—Color: Green-White Group 157A.

*Styles.*—Color: Green-White Group 157C with intonations of Red-Purple 66B. Middle of style is Red Group 47B.

PLANT

Plant growth: Compact and bushy. When grown as a 10 cm pot plant, the average height of the plant itself is 16 cm–18 cm and the average width is 18 cm–20 cm. When grown as a nursery plant on its own roots the average plant height is 25–30 cm and the average plant width is 18–22 cm.

Stems:

*Color.*—Young wood: Green Group 138B. Older wood: Green Group 138A.

*Thorns.*—Incidence: Few to nearly lacking.

*Bark.*—Young wood: Smooth. Older wood: Smooth.

Plant foliage: Normal number of leaflets on normal leaves in middle of the stem: 5 leaflets.

*Leaf size.*—Small. 55 mm (1)×30 mm (w).

*Abundance.*—Average.

*Color.*—Upper Leaf Surface: Green Group 137A. Lower Leaf Surface: Green Group to 138B. Juvenile Foliage: Green Group 137C.

Plant leaves and leaflets:

*Stipules.*—Size: 8 mm–10 mm. Margins: With hairs. Color: Green Group 137C.

*Petiole.*—Length: 15 mm–16 mm. Underneath: With small prickles. Color: Green Group 138A.

*Rachis.*—Red intonations of Greyed-Red Group 181C.

*Leaflet edge.*—Serrated.

*Shape.*—Leaflets are ovate.

*Leaflets.*—Number: 5.

*Other.*—Weak gloss on upper surface. Thin texture.

Disease resistance: Average resistance to mildew and Botrytis under normal growing conditions in Half Moon Bay, Calif. and Fredensborg, Denmark.

We claim:

1. A new and distinct variety of rose plant of the miniature class, substantially as herein illustrated and described as a distinct and novel rose variety due to its abundant flowers, attractive long lasting foliage and compact growth, year-round flowering under glasshouse conditions, suitability for production from softwood cuttings in pots, durable flowers and foliage which make the variety suitable for distribution in the floral industry.

* * * * *

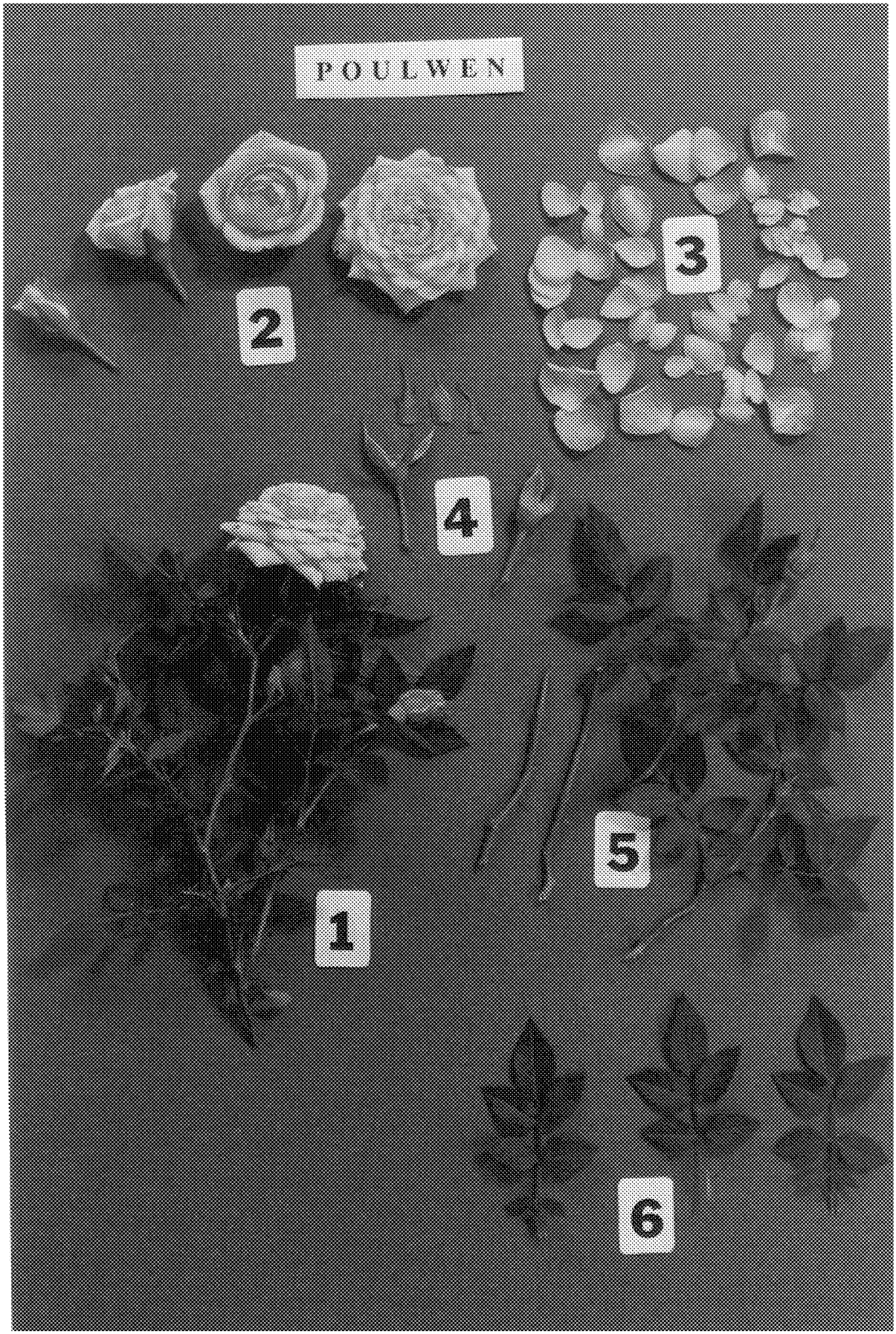
POULWEN
2
3
4
5
1
6